United States Patent

Preiss et al.

[11] 4,208,412
[45] Jun. 17, 1980

[54] β-LACTAM ANTIBIOTICS

[75] Inventors: Michael Preiss; Karl G. Metzger, both of Wuppertal, Fed. Rep. of Germany

[73] Assignee: Bayer Aktiengesellschaft, Leverkusen, Fed. Rep. of Germany

[21] Appl. No.: 900,400

[22] Filed: Apr. 26, 1978

[30] Foreign Application Priority Data

May 7, 1977 [DE] Fed. Rep. of Germany ....... 2720580

[51] Int. Cl.² ............... A61K 31/40; A61K 31/415; A61K 31/43; C07D 499/80
[52] U.S. Cl. .................. 424/250; 260/239.1; 424/246; 424/263; 424/267; 424/271; 544/22; 544/25; 544/27; 544/28
[58] Field of Search .............. 260/239.1; 424/250, 424/263, 267, 271

[56] References Cited
U.S. PATENT DOCUMENTS

| | | | |
|---|---|---|---|
| 3,959,258 | 5/1976 | König et al. | 260/239.1 |
| 3,974,142 | 8/1976 | König et al. | 260/239.1 |
| 4,087,424 | 5/1978 | Saikawa et al. | 260/239.1 |

Primary Examiner—Bernard Helfin
Assistant Examiner—Vera C. Clarke
Attorney, Agent, or Firm—Sprung, Felfe, Horn, Lynch & Kramer

[57] ABSTRACT

β-Lactam compounds of the formula

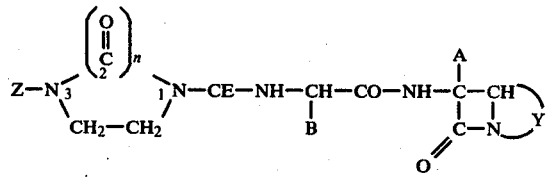

in which
  A is hydrogen or methoxy,
  B is phenyl; phenyl substituted by at least one of hydroxyl, halogen, methoxy, -CN and $CH_3$-$SO_2$-; thienyl; cyclohexenyl; 1,4-cyclohexadien-1-yl; or furyl;
  E is oxygen or sulphur;
  n is 1 or 2,
  Y is

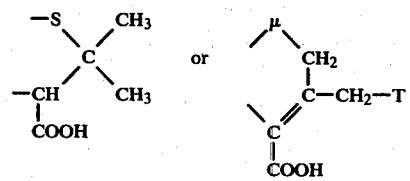

or a salt thereof, in which
  the carbon atom which carries the carboxyl group is bonded to the nitrogen atom of the β-lactam ring,
  T is hydrogen, alkyl-CO—O—, hydroxyl-, pyridinium, aminopyridinium, carbamoyloxy, azido, cyano, optionally N-substituted thiocarbamoylthio, optionally substituted S-phenyl, or a —S—Het group,
  Het is an optionally substituted heterocyclic 5-membered or 6-membered ring;
  U is oxygen, sulphur or —$CH_2$—; and
  Z is an optionally substituted aromatic or pseudoaromatic ring which contains at least one nitrogen atom via which it is bonded to the $N_3$ of the imidazolidinone radical of the β-lactam, are suitable as antibiotics, growth promoters for animals and preservatives.

7 Claims, No Drawings

β-LACTAM ANTIBIOTICS

The present invention relates to certain new β-lactam compounds, to a process for their production and to their use as medicaments, in particular as antibacterial agents and as agents for promoting growth and for improving feedstuff utilisation in animals.

β-Lactam compounds substituted in a particular manner, such as α-(imidazolidin-2-oxo-1-yl-carbonylamino)-benzylpenicillins substituted in a particular manner, and corresponding cephalosporins having an imidazolidin-2-oxo-1-yl-carbonylamino side chain are known from German Offenlegungsschriften Nos. (German Published Specifications) 2,104,580, 2,152,967, 2,258,973, 2,402,465 and 2,428,139.

The present invention provides compounds which are β-lactams of the following general formula I or their salts:

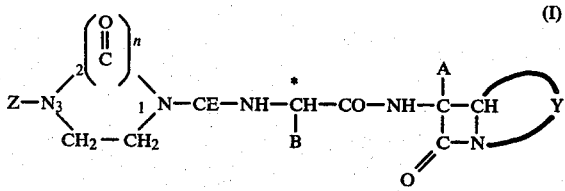 (I)

in which
A is hydrogen or methoxy;
B is phenyl optionally substituted by hydroxyl, halogen, methoxy, —CN and/or CH$_3$—SO$_2$—; thienyl; cyclohexenyl; 1,4-cyclohexadien-1-yl; or furyl;
E is oxygen or sulphur;
n is an integer having a value of 1 or 2;
Y is a group of the formula

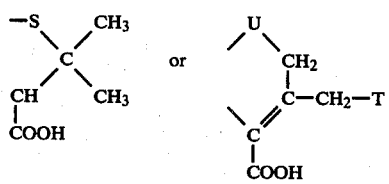

in which
the carbon atom which carries the carboxyl group is bonded to the nitrogen atom of the β-lactam ring and T is hydrogen, alkyl —CO—O—, hydroxyl, pyridinium, aminopyridinium, carbamoyloxy, azido, cyano, thiocarbamoylthio, optionally substituted —S-phenyl, or a —S-Het group, in which Het represents an optionally substituted heterocyclic 5-membered or 6-membered ring, and U is oxygen, sulphur or —CH$_2$—; and
Z represents an optionally substituted, aromatic or pseudo-aromatic ring which contains at least one nitrogen atom, via which it is bonded to the N$_3$ of the imidazolidinone radical of the β-lactam;
said β-lactams of the formula (I) being in either of the two possible configurations R and S in respect of the chirality center $\overset{*}{C}$ or in the form of mixtures in said R and S configurations, and optionally in the form of mixtures of the diastereomers resulting therefrom.

The new β-lactam compounds according to the invention differ from the known compounds of the state of the art in that the N$_3$ of the imidazolidinone radical is directly bonded, that is to say without an intermediate member, such as for example, a carbonyl or sulphonyl group, to a N atom of a cyclic radical.

The compounds according to the invention have powerful antibacterial properties and possess the property of improving growth and feedstuff utilization in animals.

In a further aspect the present invention provides a process for the production of a compound of the invention in which a compound of the general formula (II):

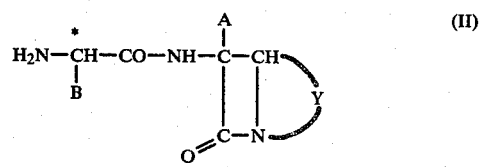 (II)

in which A, B, $\overset{*}{C}$ and Y have the same meaning as defined hereinbefore in formula I; or a derivative thereof obtained by silylation on the carboxyl group or on the carboxyl and primary amino group, is reacted with a compound of the general formula (III):

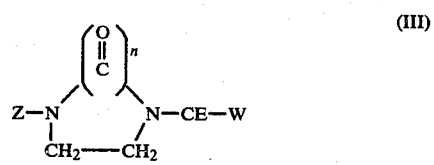 (III)

in which
Z, E and n have the same meaning as defined hereinbefore in Formula (I), and
W is halogen, azide or another nucleofugic leaving group, optionally in the presence of a solvent and/or an acid-binding agent preferably at a temperature of from −20° C. to +50° C., and, where a silylated derivative of a compound of formula (II) has been used, splitting off the silyl group(s), and optionally converting the resulting β-lactam of formula (I) or salt thereof into a salt thereof or the corresponding free β-lactam of formula (I), respectively.

Surprisingly, the new β-lactam compounds exhibit a very good activity against a broad spectrum of pathogens, in addition to being well tolerated. The substances according to the invention thus represent an enrichment of pharmacy.

If D-α-amino-benzylpenicillin and 1-chlorocarbonyl-2-oxo-3-(2,5-dimethyl-1-pyrrolyl)-imidazolidine are used as starting materials, the course of the reaction can be represented by the following reaction equation:

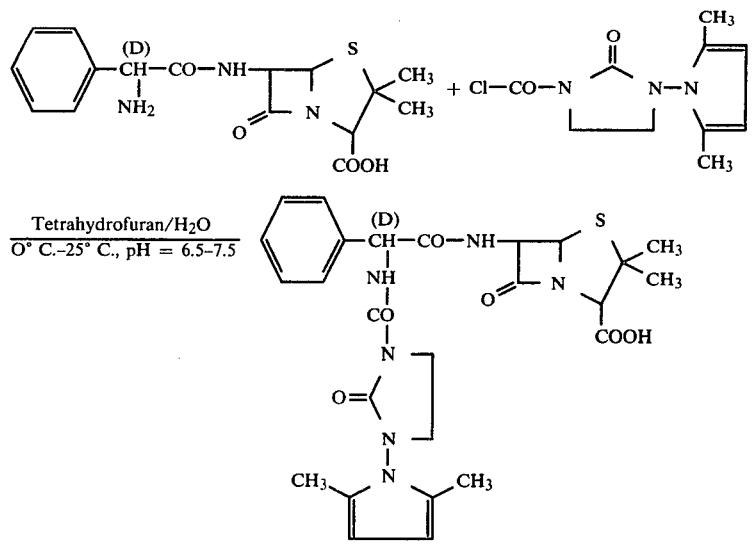

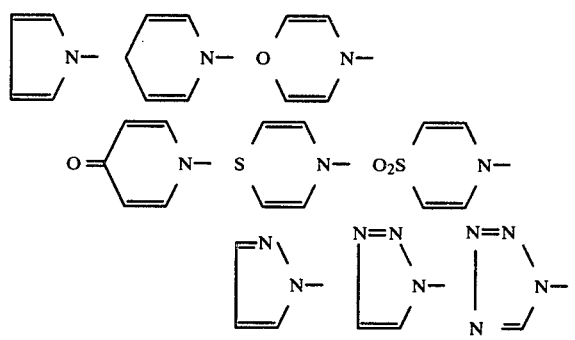

In the formulae I and III, Z may denote optionally substituted

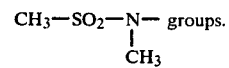

The heterocyclic rings Z can be monosubstituted, di-substituted or tri-substituted, preferably mono-substituted or di-substituted, most preferably mono-substituted. Examples of substituents which may be mentioned are: lower alkyl, in particular methyl, ethyl, propyl, isopropyl and t-butyl, preferably methyl; lower alkylidene, in particular methylene, ethylidene and isopropylidene; vinyl, propenyl, allyl and isopropenyl; lower alkoxymethyl, in particular methoxymethyl; lower alkylthiomethyl, in particular methylthiomethyl; trifluoromethyl; hydroxymethyl; formyl; lower alkanoyl, in particular acetyl; lower alkanoyloxymethyl, in particular acetoxymethyl; benzyl; aryl, in particular phenyl; cyanomethyl; the $CH_3$—NH—CO—$CH_2$— and $(CH_3)_2N$—CO—$CH_2$— groups; lower alkoxycarbonyl, in particular methoxycarbonyl and ethoxycarbonyl; carboxyl; cyano; hydroxyl; lower alkanoyloxy, in particular acetoxy; lower alkoxy, in particular methoxy and ethoxy, benzyloxy; halogen, in particular fluorine, chlorine and bromine, preferably chlorine; mercapto; lower alkylthio, in particular methylthio and ethylthio; lower alkylsulphinyl, in particular methylsulphinyl and ethylsulphinyl; lower alkylsulphonyl, in particular methylsulphonyl and ethylsulphonyl; and the $CH_3$—CO—NH—, $CH_3$—CO—N($CH_3$)—, $CH_3$—$SO_2$—NH— and $$CH_3-SO_2-\underset{\underset{CH_3}{|}}{N}- \text{ groups.}$$

The 1-pyrrolyl radicals Z are particularly preferred.

The heterocyclic rings Z are very particularly preferably unsubstituted, monosubstituted or disubstituted, lower alkyl, trifluoromethyl, lower alkylsulphonyl and lower alkylthio being mentioned as preferred substituents.

A particularly preferably represents hydrogen and E particularly preferably represents oxygen. U particularly preferably denotes sulphur.

In the definition of T, alkyl in alkyl—CO—O— preferably denotes alkyl with 1 to 4, in particular 1 or 2, carbon atoms. Examples which may be mentioned are methyl and ethyl, preferably methyl. T particularly preferably represents hydrogen, OH or methyl—CO—O—.

The thiocarbamoylthio radical (in the definition of T) can be substituted on the N atom by one or two lower alkyl radicals. Furthermore, this N atom can be a constituent of a pyrrolidine, piperidine, morpholine and $N^4$-lower alkylpiperazine ring.

The heterocyclic ring Het in —S-Het (in the definition of T) consists of 5 or 6 ring members and contains from 1 to 4, preferably from 2 to 4 and very particularly preferably 3 or 4, identical or different hetero-atoms, each of which is oxygen, sulphur or nitrogen. The heterocyclic ring is preferably unsaturated and particularly preferably contains 2 double bonds. The heterocyclic ring can contains one or more, preferably 1 or 2, in particular one, substituents. Examples of substituents which may be mentioned are: fluorine, chlorine, bromine and iodine, preferably chlorine or bromine; amino, lower alkylamino, and di-lower alkylamino; lower alkyl; cycloalkyl (having from 3 to 7, preferably 5 or 6, carbon atoms in the cycloalkyl moiety); lower alkyloxy; trifluoromethyl; phenyl; benzyl; and acylamino having preferably from 2 to 5, in particular 2 or 3 carbon atoms. Particularly preferred examples of —S-Het which may be mentioned are:

$$-S-\underset{\underset{CH_3}{|}}{\overset{N\text{———}N}{\underset{N}{\|}}} \quad -S-\overset{N\text{———}C-R^1}{\underset{X}{\|}} \text{ in which } R^1 \text{ is H, CH}_3, \text{ or}$$

$$C_2H_5 \text{ and X is O or S,} \quad -S-\overset{N\text{———}N}{\underset{X}{\|}}-R^2$$

in which $R^2$ is H, $CH_3$, $CF_3$, $NHCH_3$, NHCHO, $N(CH_3)_2$ or $NHCOCH_3$, and X is O or S; and $$-S-\overset{N\text{———}N-R^3}{\underset{N}{\|}}$$

in which $R^3$ is H or $CH_3$.

The —S—phenyl radical in the definition of T can carry one or more, preferably from 1 to 3, in particular 1 or 2, identical or different substituents, preferred substituents being those which are listed above as being possible substituents of the radical —H—Het.

Nucleofugic leaving groups in the definition of W are to be understood as all the nucleofugic groups customarily used in organic chemistry, and above all those which are described in Angewandte Chemie, 81 (1969), page 543.

The phenyl radical B can carry one or more identical or different, preferably from 1 to 3, in particular 1 or 2 and most preferably 1, substituent(s) each of which is hydroxyl, halogen, methoxy, —CN or $CH_3$—$SO_2$—. In the case of monosubstitution, the substituent is preferably in the 4-position (relative to the bond of the phenyl radical on the asymmetric carbon atom $\overset{*}{C}$).

Halogen as a substituent in the phenyl radical B denotes fluorine, chlorine, bromine and iodine, preferably fluorine, chlorine or bromine, in particular fluorine or chlorine.

B particularly preferably represents phenyl, 4-hydroxyphenyl and 1,4-cyclohexadien-1-yl.

Among the new β-lactam salts of the invention, those salts that are pharmaceutically acceptable are particularly important and are preferred.

Pharmaceutically acceptable salts of the compounds of the formula I are salts of these compounds with inorganic and organic bases on the acid carboxyl group or on the acid carboxyl and sulphonyl groups. Bases which can be employed for this are all the bases customarily used in pharmaceutical chemistry, in particular in the chemistry of antibiotics. Examples of inorganic bases which may be mentioned are: alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate, and sodium bicarbonate and potassium bicarbonate; and aluminum hydroxide and ammonium hydroxide. Organic bases which can be used are primary, secondary and tertiary aliphatic amines and heterocyclic amines. Examples which may be mentioned are: di- and tri-lower alkylamines, for example diethylamine and triethylamine, tri-β-hydroxyethylamine, procaine, dibenzylamine, N,N'-dibenzylethylenediamine, N-benzyl-β-phenyl-ethylamine, N-methyl- and N-ethyl-morpholine, 1-ephenamine, dehydroabietylamine, N,N'-bis-dehydroabietylethylenediamine and N-lower alkylpiperidine. So-called basic aminoacids, such as lysine or arginine, can also be advantageously used as bases. Particularly preferred salts are the sodium salts.

By the expression "lower alkyl" there is to be understood herein, in each case, straight-chain or branched alkyl having from 1 to 5, preferably 1 to 3, in particular 1 or 2, carbon atoms. In connection with other groups, such as in "di-lower alkylamino", the above definition of "-lower alkyl-" only relates to the alkyl moiety of the group concerned.

Particularly preferred compounds of the general formula I are those in which

A is hydrogen;
B is phenyl, hydroxyphenyl (particularly preferably p-hydroxyphenyl) or 1,4-cyclohexadien-1-yl;
E is oxygen;
Y represents a group of the formula $$-\overset{|}{\underset{COOH}{CH}}-\overset{S}{\underset{}{\diagdown}}\overset{CH_3}{\underset{CH_3}{\diagup}} \quad \text{or} \quad \overset{S}{\underset{\underset{COOH}{|}}{\diagdown}}\overset{CH_2}{\underset{C}{\diagup}}\overset{}{\underset{}{\diagdown}}C-CH_2-T$$

wherein
T is —O—CO—$CH_3$, —OH, 1-methyl-tetrazol-5-yl-thio, 2-methyl-1,3,4-thiadiazol-5-yl thio or 3-methyl-1,2,4-thiadiazol-5-yl-thio, and Z is unsubstituted, monosubstituted or disubstituted 1-pyrrolyl, and
$\overset{*}{C}$ is in the D—=R-configuration, and the salts, especially the sodium salts of these compounds.

All the crystal forms and hydrate forms of the compounds of the general formula I according to the invention and their salts are antibacterially active in the same manner.

The compounds of the general formula II which can be used according to the invention are already known or are obtainable by known methods (compare, for example, E. H. Flynn, Cephalosporins and Penicillins, Academic Press, New York and London, 1972).

Examples which may be mentioned are: α-aminobenzylpenicillin (short name: ampicillin), α-amino-p-hydroxybenzylpenicillin (short name: amoxicillin), α-amino-p-methylbenzylpenicillin, α-amino-p-chlorobenzylpenicillin, 6-(2-amino-2-(1,4-cyclohexadien-1-yl;)-acetamido)-penicillanic acid (short name: epicillin), 7-(α-amino-phenylacetamido)-3-methyl-ceph-3-em-4-carboxylic acid, 7-(α-amino-phenylacetamido)-3-acetoxymethyl-ceph-3-em-4-carboxylic acid (short name: cephaloglycine), 7-(α-amino-phenylacetamido)-3-((1-methyltetrazol-5-yl)-thio-methyl)-ceph-3-em-4-carboxylic acid, 7-(α-aminophenylacet-amido)-3-((2-methyl-1,3,4-thiadiazol-5-yl)-thiomethyl)-ceph-3-em-4-carboxylic acid as well as the sodium salts and the mono- and di-(trimethylsilyl) derivatives of these compounds.

All the crystal forms, hydrate forms and salts of the compounds of the general formula II are suitable starting materials for the process according to the invention.

The compounds of the general formula III used as starting materials are known or are obtainable by known methods. For example, they can be prepared in the customary manner by reacting a heterocyclic compound of the general formula IV:

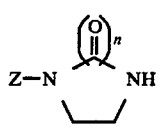
(IV)

in which n is 1 or 2 and Z has the same meaning as defined hereinbefore in formula I, with, for example a molar amount of a compound of the general formula W—CE—W, in which W and E have the same meaning as defined hereinbefore in formula III, such as, for example, phosgene or thiophosgene, in an inert organic solvent, such as, for example, tetrahydrofuran, or in a mixture of water and an inert organic solvent, such as, for example, chloroform, at a temperature of from 0° to 25° C. optionally in the presence of a molar amount of a base, such as, for example, triethylamine, and by customary working up and purification.

The preparation of the respective compounds of the general formula IV and III is indicated in each case in the examples, unless they are described in the literature. In general the remaining starting compounds are all readily available in an analogous manner.

Examples of compounds of formula III which may be mentioned are:

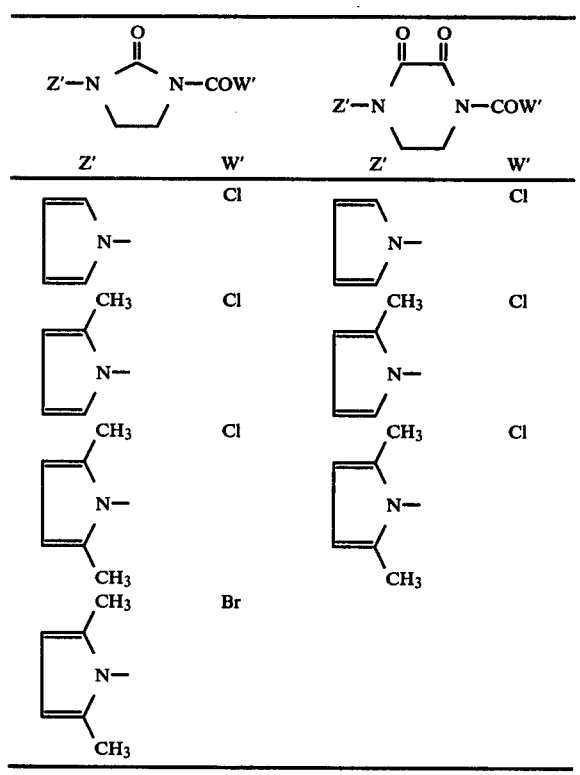

Diluents which can be used in the reaction, according to the invention, of the compounds of the formulae II and III, are water and virtually all the customary inert organic solvents, optionally mixed with water.

If the non-silylated compounds of the general formula II are used for the reaction with the compounds of the general formula III, this reaction can be carried out, for example, in any desired mixtures of water and those organic solvents which are water-miscible, for example ketones, such as acetone, cyclic ethers, for example tetrahydrofuran and dioxane, nitriles, for example acetonitrile, formamides, for example dimethylformamide, dimethylsulphoxide or alcohols, for example isopropanol. In this procedure, the pH of the reaction mixture is kept, for example, at from 6.5 to 8.0 by adding bases or using buffer solutions (for example phosphate buffers or citrate buffers). However, the process according to the invention can also be carried out at a pH of from pH 1.5 to 9.5, for example from 4.5 to 9.0, or at from pH 2.0 to 4.5. Furthermore, it is possible to carry out the reaction in a solvent which is not water-miscible, for example a halogenated hydrocarbon, such as chloroform or methylene chloride, a base, preferably triethylamine, diethylamine or N-ethylpiperidine, being added desirably. Furthermore, the reaction can be carried out in a mixture of water and a solvent which is not water-miscible, such as, for example, an ether, for example diethyl ether, halogenated hydrocarbon, for example chloroform and methylene chloride, carbon disulphide, ketone, for example isobutyl methyl ketone, ester, for example ethyl acetate, aromatic solvent, for example benzene, and the like, it being appropriate to stir the mixture vigorously and to keep the pH value at from 1.5 to 9.5, preferably from 4.5 to 9.0 or, for example, from 2.0 to 3.0, by adding bases or using buffer solutions. However, it is also possible to carry out the reaction in water alone in the absence of an organic solvent in the presence of an organic or inorganic base or with the addition of buffer substances.

Suitable silyl radicals for the derivatives of the compounds of the general formula II are all the silyl groups which are described in the literature and are used for similar purposes. It is known of some of these silyl groups, for example of the trimethylsilyl group, that they are rapidly split off by water or solvents containing HO groups. On the other hand, it is known of other silyl groups, for example of the dimethoxy-methyl-silyl group or of the dimethyltert.-butyl-silyl group, that they are substantially more resistant hydrolysis. Depending on the nature of the silyl radicals used, the reaction must therefore be carried out in a solvent which is completely anhydrous and free from hydroxyl groups. If monosilylated compounds of the general formula II are used for the reaction with the compounds of the general formula III, it is possible to carry out the reaction with or without, though preferably with, the addition of a base.

If disilylated derivatives of compounds of the general formula II are used, it is possible to carry out the reaction with or without, though preferably without, the addition of a base.

All the inorganic and organic bases customarily employed in organic chemistry can be used as the base, including bases such as alkali metal hydroxides and alkaline earth metal hydroxides, alkaline earth metal oxides, alkali metal carbonates and alkaline earth metal carbonates and bicarbonates, ammonia, primary, secondary and tertiary aliphatic and aromatic amines and heterocyclic bases. Examples which may be mentioned are sodium hydroxide, potassium hydroxide and calcium hydroxide, calcium oxide, sodium carbonate and potassium carbonate, sodium bicarbonate and potassium bicarbonate, ethylamine, methyl-ethylamine, triethylamine, hydroxyethylamine, aniline, pyridine and piperidine.

Suitable buffer mixtures are all the buffer mixtures customarily used in organic chemistry, such as phosphate buffers, citrate buffers and tris-(hydroxymethyl) aminomethane buffers.

In the reaction of the compounds of formulae II and III, the reaction temperatures can be varied within a relatively wide range.

In general, the reaction is carried out at from −20° C. to +50° C., preferably from 0 to +25° C. As in the case of most chemical reactions, temperatures which are higher or lower than those indicated can also be used. However, if the values indicated are exceeded considerably, side reactions which lower the yield or have an adverse influence on the purity of the products take place to an increasing extent. On the other hand, reaction temperatures which are lowered excessively reduce the rate of reaction so severely that reductions in yield can occur.

The reaction can be carried out under normal pressure, but also under reduced or elevated pressure. In general, the reaction is carried out under ambient pressure.

In carrying out the process according to the invention, the reactants can be reacted with one another in equimolar amounts. However, in certain circumstances it can be appropriate to use one of the two reactants in excess, in order to facilitate the purification of the desired β-lactam antibiotic or its preparation in the pure state, and to increase the yield.

For example, it is possible to employ the reactants of the general formula II in an excess of from 0.1 to 0.3 molar equivalents and thereby to achieve less decomposition of the reactants of the general formula III in a water-containing solvent mixture. Because of their good solubility in aqueous mineral acids, the excess of the reactants of the general formula II can be easily removed during the working up of the reaction mixture.

On the other hand, however, the reactants of the general formula III can also be advantageously employed in an excess of, for example, 0.1 to 1.0 molar equivalents. By this procedure, the reactants of the general formula II are better utilized and the decomposition of the reactants of the general formula III, which proceeds as a side reaction in water-containing solvents, is compensated. Since the compounds of the general formula III added in excess are rapidly converted in water into neutral nitrogen-containing heterocyclic compounds, which can be easily removed, the purity of the β-lactam compounds is scarcely impaired by this procedure.

Bases can be added in equimolar amounts, but also in excess, with respect to the reactants of the formulae II and III. The amount of base used depends, of course, on the chosen range of pH values to be maintained.

The working up of the reaction mixtures for the preparation of the β-lactam compounds according to the invention and their salts and the purification of these compounds may be carried out in the manner which is generally customary for penicillins and cephalosporins, for example, by removing the solvent, taking up the residue in an organic solvent(s) and precipitating and recrystallizing the products.

The sodium salts may be obtained from an ethereal solution of the free acids in a particularly advantageous manner by precipitation with sodium 2ethylhexanoate.

If the monosilylated or disilylated compounds of the general formula II are used in the reactions according to the invention, the hydrolytic splitting off of the silyl radicals or radical occurs in the course of the aqueous working up of the reaction mixtures, optionally at an acid pH. Specific new active compounds which may be mentioned are compounds of formulae V, VI, VII and VIII:

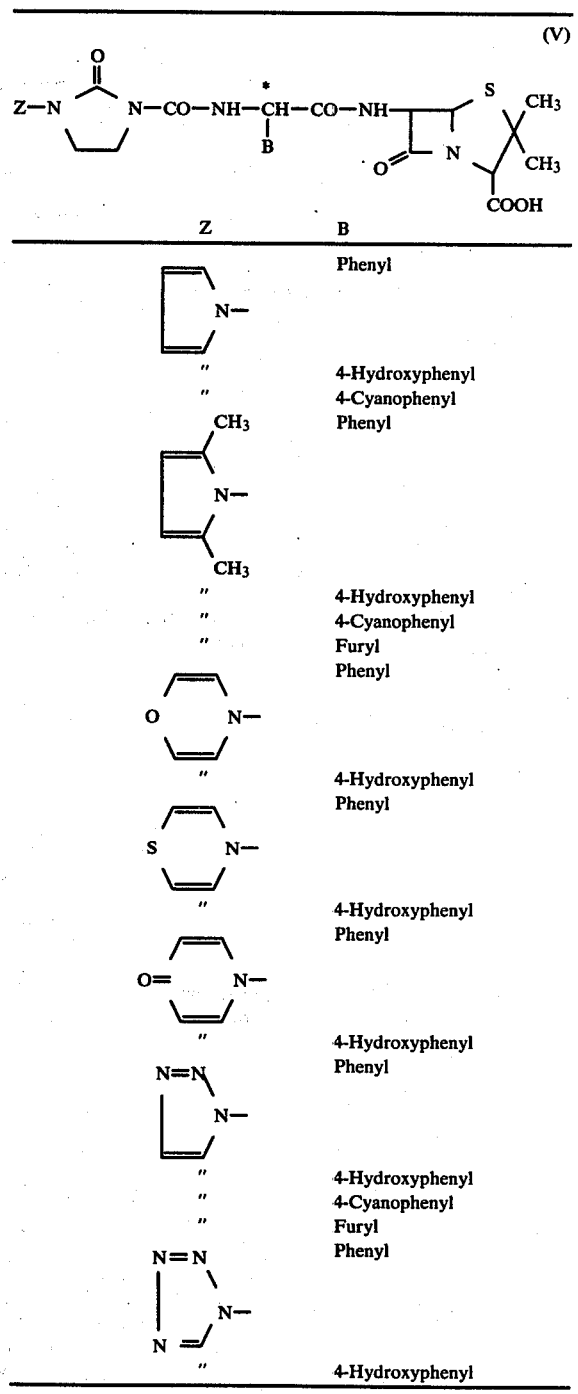

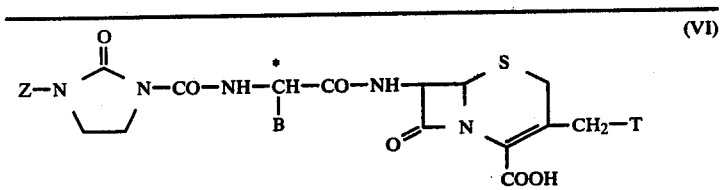
(VI)
| Z | B | T |
|---|---|---|
| 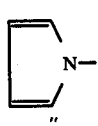 | Phenyl | —O—CO—CH₃ |
| " | " | 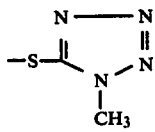 |
| " | " | 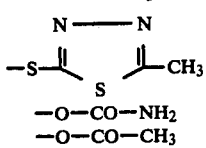 |
| " | " | —O—CO—NH₂ |
| 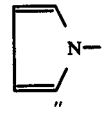 | 4-Hydroxyphenyl | —O—CO—CH₃ |
| " | " | 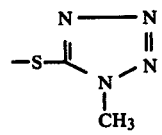 |
| " | " | 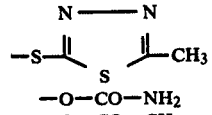 |
| " | " | —O—CO—NH₂ |
|  | Furfuryl | —O—CO—CH₃ |
| " | " | 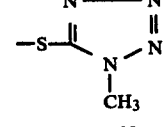 |
| " | " | 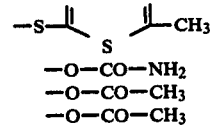 |
| " | " | —O—CO—NH₂ |
| " | Cyanophenyl | —O—CO—CH₃ |
|  | Phenyl | —O—CO—CH₃ |
| " | " | 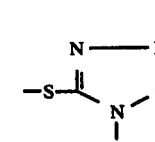 |
| " | " | 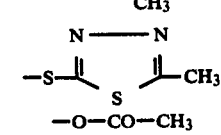 |
| " | 4-Hydroxyphenyl | —O—CO—CH₃ |

-continued

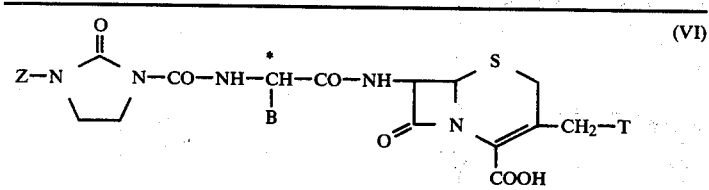

| Z | B | T |
|---|---|---|
| " | " | -S-C(=N-N=N-N(CH₃)) (1-methyl-tetrazol-5-yl-thio) |
| " | " | -S-C(=N-N=C(CH₃)-S) (5-methyl-1,3,4-thiadiazol-2-yl-thio) |
| " | " | —O—CO—NH₂ |
| (pyrrol-1-yl) N— | Furfuryl | —O—CO—CH₃ |
| " | " | -S-(1-methyl-tetrazol-5-yl) |
| " | " | -S-(5-methyl-1,3,4-thiadiazol-2-yl) |
| " | " | —O—CO—NH₂ |
| " | Cyanophenyl | —O—CO—CH₃ |
| (2,5-dimethylpyrrol-1-yl) CH₃–N–CH₃ | Phenyl | —O—CO—CH₃ |
| " | " | -S-(1-methyl-tetrazol-5-yl) |
| " | " | -S-(5-methyl-1,3,4-thiadiazol-2-yl) |
| " | 4-Hydroxyphenyl | —O—CO—CH₃ |
| " | " | -S-(1-methyl-tetrazol-5-yl) |
| " | " | -S-(5-methyl-1,3,4-thiadiazol-2-yl) |
| (2,5-dimethylpyrrol-1-yl) CH₃–N–CH₃ | 4-Cyanophenyl | —O—CO—CH₃ |
| " | Furfuryl | —O—CO—CH₃ |

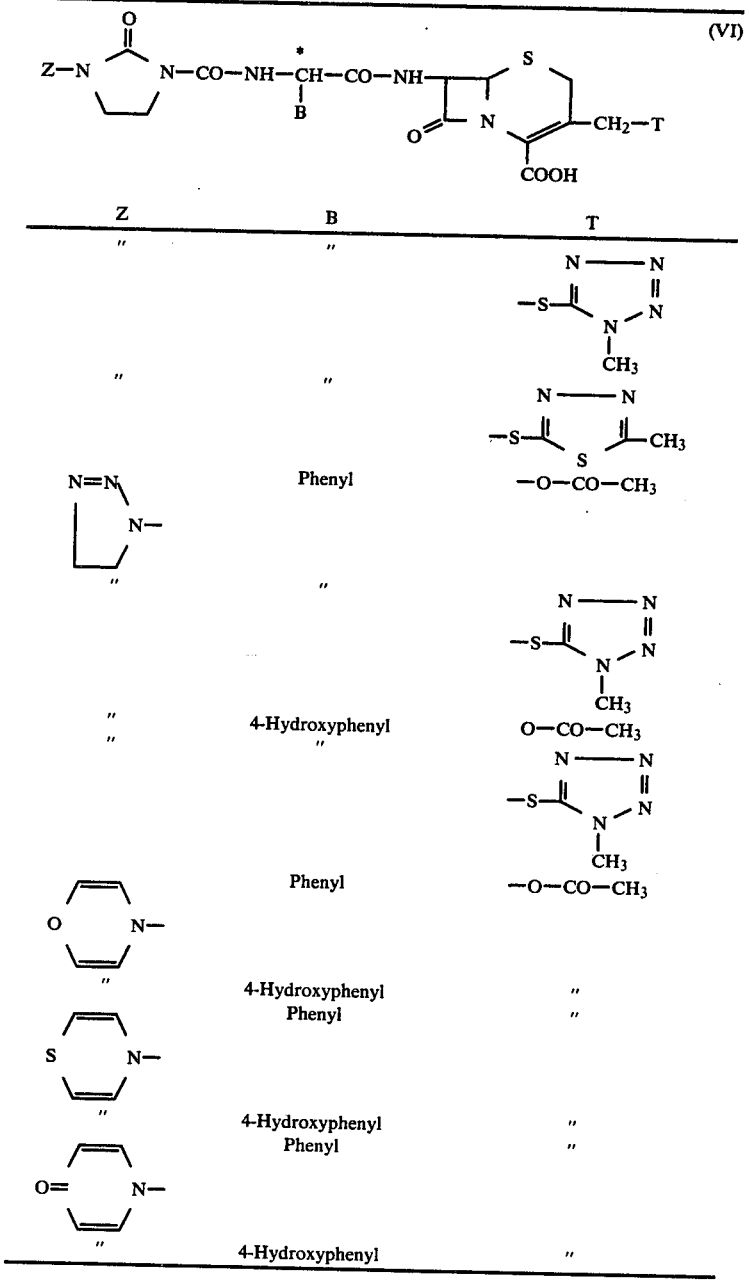
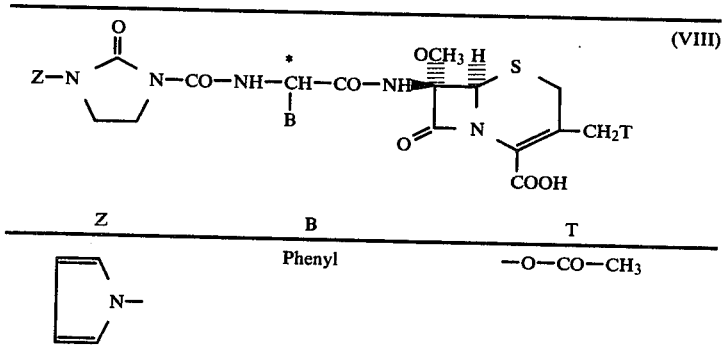

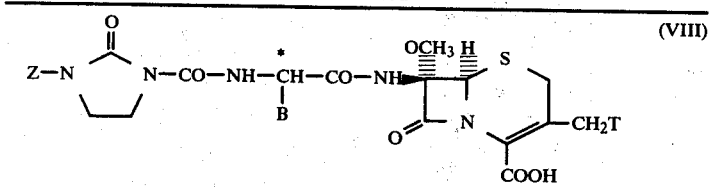

| Z | B | T |
|---|---|---|
| (2,5-dimethylpyrrol-1-yl) | " | " |
| (4,5-dihydro-1,2,3-triazin-2-yl) | " | " |
| (morpholin-4-yl) | " | " |
| (thiomorpholin-4-yl) | " | " |

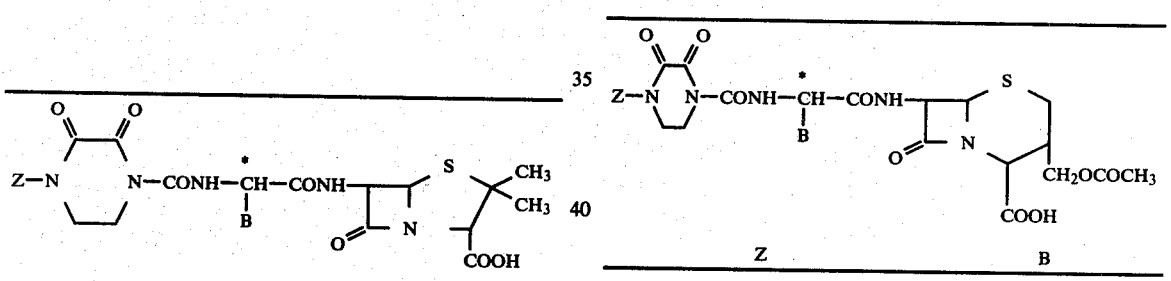

| Z | B |
|---|---|
|  | Phenyl |
| (pyrrol-1-yl) | " |
| (2,5-dimethylpyrrol-1-yl) | " |
| (4,5-dihydro-1,2,3-triazin-2-yl) | " |
| (morpholin-4-yl) | " |
| (thiomorpholin-4-yl) | " |

| Z | B |
|---|---|
|  | Phenyl |
| (pyrrol-1-yl) | " |
| (2,5-dimethylpyrrol-1-yl) | " |
| (4,5-dihydro-1,2,3-triazin-2-yl) | " |
| (morpholin-4-yl) | " |
| (thiomorpholin-4-yl) | " |

If in the radicals Z in the compounds of general formulae I and III one or more asymmetric centers or cisand trans-forms occur, it should be understood that all the possible R—, S—, cis— and trans-forms and all the possible combinations of these forms of the compounds of general formulae I and III are included in references to compounds of said formulae unless the contrary is stated.

The compounds according to the invention display a powerful antimicrobial activity, coupled with low toxicity and good tolerance. These properties enable the compounds to be used as active ingredients in medicine and as substances for preserving inorganic and organic materials, especially organic materials of all kinds, for example polymers, lubricants, paints, fibers, leather, paper and timber, and of foodstuffs and water.

The compounds according to the invention are active against a very broad spectrum of micro-organisms. With their aid it is possible to combat, for example, Gram-negative and Gram-positive bacteria and bacteria-like micro-organisms and to prevent, alleviate and/or cure diseases caused by these pathogens.

The compounds according to the invention are particularly active against bacteria and bacteria-like micro-organisms. They are therefore particularly suitable for the prophylaxis and chemotherapy of local and systemic infections caused by these pathogens, in human medicine and veterinary medicine.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermidis, Staph. aerogenes* and *Gaffkya tetragena* (Staph.=Staphylococcus);

Lactobacteriaceae, such as Streptococci, for example Streptococcus pyogenes, α- and β-haemolysing Streptococci, non-(γ-)-haemolysing Streptococci, *Str. viridans, Str. faecalis* (Enterococci), *Str. agalactiae, Str. lactis, Str. equi, Str. anaerobis* and *Diplococcus pneumoniae* (Pneumococci) (Str.=Streptococcus);

Neisseriaceae, such as Neisseriae, for example *Neisseria gonorrhoeae* (Gonococci), *N. meningitidis* (Meningococci), *N. catarrhalis* and *N. flava* (N.—Neisseria);

Corynebacteriaceae, such as Corynebacteria, for example *Corynebacterium diphtheriae, C pyogenes, C. diphtheroides* and *C. acnes* (C.=Corynebacterium);

Enterobacteriaceae, such as Escherichiae bacteria of the Coli group, Escherichia bacteria, for example *Escherichia coli,* Enterobacter bacteria, for example *E. aerogenes. E. cloacae,* Klebsiella bacteria, for example *K. pneumoniae* and *K. ozaenae,* and Serratia, for example *Serratia marcescens* (E.=Enterobacter) (K.=Klebsiella), Proteae bacteria of the Proteus group, Proteus, for example *Proteus vulgaris, Pr. morganii, Pr. rettgeri* and *Pr. mirabilis* (Pr.=Proteus), Providencia, for example Providencia sp., Salmonelleae, Salmonella bacteria, for example *salmonella paratyphi* A and B, *S.* typhi, *S. enteritidis, S. cholerae suis* and *S. typhimurium* (S.=Salmonella), and Shigella bacteria, for example *Shigella dysenteriae, Sh. ambigua, Sh. flexneri, Sh. boydii* and *Sh. sonnei* (Sh.=Shigella);

Pseudomonadaceae, such as Pseudomonas bacteria, for example *Pseudomonas aeruginosa,* and Aeromonas bacteria, for example *Aeromonas liquefaciens;*

Spirillaceae, such as Vibrio bacteria, for example *Vibrio cholerae,*

Parvobacteriaceae or Brucellaceae, such as Pasteurella bacteria, for example *Pasteurella multocida,* Haemophilus bacteria, for example *Haemophilus influenzae,* and Bordetella bacteria, for example *B. bronchiseptica* (B.=Bordetella), Bacteroidacea, such as Bacteroides bacteria, for example *Bacteroides fragilis,* Fusiforme bacteria, for example *Fusobacterium fusiforme* and Sphaerophorus bacteria, for example *Sphaerophorus necrophorus, Sph. necroticus* and *Sph. pyrogenes* (Sph.=Sphaerophorus);

Bacillaceae, such as aerobic spore-forming Bacillaceae for example *Bacillus anthracis, B. subtilis* and *B. cereus* (B.=Bacillus), and anaerobic spore-forming Clostridia, for example *Clostridium perfringens;*

The above list of pathogens is purely by way of example and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis and arthritis.

As stated above, the invention also relates to the use in human and veterinary medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is from 300 mg to 40 g, desirably from 750 mg to 15 g of active ingredient.

The production of the above mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, or intravenously), rectally or locally, preferably parenterally especially intravenously or intramuscularly. Preferred pharmaceutical compositions and medicaments are therefore those adapted for parenteral administration, such as injection solutions and suspensions. Administration in the method of the invention is preferably parenteral.

In general it has proved advantageous to administer amounts of from 6 mg to 800 mg, preferably from 15 to 300 mg, per kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above mentioned minimum dosage rate, while in other cases the upper limit mentioned must be exceeded to achieve the desired results. Where larger amounts are administered it can be advisable to divide these into several, for example 3, individual administrations over the course of the day. Advantageously each individual administration contains from 2 to 300, preferably from 10 to 150, mg/kg of body weight.

When used as feedstuff additives, the new compounds can be administered in the customary manner together with the feedstuff or with feedstuff formulations or with the drinking water. By this means it is possible to prevent an infection by Gram-negative or Gram-positive bacteria and also to achieve better utilization of the feedstuff.

The new β-lactam compounds are distinguished by powerful antibacterial actions, which have been tested in vivo and in vitro, and by oral resorbability.

The β-lactam compounds according to the invention can, in order to broaden the spectrum of action or to achieve a more powerful action, also be combined with, for example, amino-glycoside antibiotics, such as gentamycin, sisomycin, kanamycin, amicacin or tobramycin. Isoxazolyl-penicillins (for example oxacillin and dicloxacillin) can also be used as combination partners.

The activity of the β-lactam compounds according to the invention can be demonstrated, by way of example, by the following in vitro and in vivo experiments:

(a) In vitro experiment

The compounds from Examples 3 and 4 hereinbelow, which can be regarded as typical representatives of the compounds according to the invention, were diluted to a content of 100 μg/ml with Müller-Hinton nutrient broth. In each case, the nutrient solution contained $1 \times 10^5$ to $2 \times 10^5$ bacteria per milliliter. The small tubes containing this batch were in each case incubated for 24 hours and the degree of turbidity was then determined. Freedom from turbidity indicates action. At a dosage of 100 μg/ml, the following bacterial cultures were free from turbidity (sp. - species):

*Klebsiella pneumoniae: Enterobacter aerogenes* sp.; *Serratia marcescens; Escherichia coli* BE; *Salmonella* sp.; *Shigella* sp.; *Proteus*, indole-negative and indole-positive sp; *Pasteurella pseudotuberculosis; Haemophilus influenzae; Bordetella bronchiseptica; Staphylococcus aureus* 133; *Neisseria catarrhalis* sp.; *Diplococcus pneumoniae* sp.; *Streptococcus pyogenes* W.; and *Enterococcus* sp.;

*Lactobacillus* sp.; *Corynebacterium diphtheriae gravis; Corynebacterium pyogenes* M; *Clostridium botulinum* and *Clostridium tetani.* (b) In vivo experiment Table 1 which follows shows the action of one of the new β-lactam compounds, which can be regarded as typical compounds according to the invention, against some bacteria in an animal experiment using white mice. White mice of the CF$_1$ strain were infected intraperitoneally with the particular strain of bacteria indicated.

Table 1

| Animal experiment using white mice: | |
|---|---|
| Determination of the ED$_{100}$ after 24 hours | |
| Germ | Dose in mg of the compound from Example 3 per kg body weight (subcutaneously) |
| *Escherichia coli* C 165 | 1 × 200 |
| *Klebsiella* | 2 × 150 |
| Therapy administration: | 30 minutes after infection |
| 2 administration: | (a) 30 minutes after infection |
| | (b) 90 minutes after infection |

The ED$_{100}$ is the dose at which 100% of the infected animals still survive after 24 hours.

The process according to the invention may be illustrated by the examples which follow:

The α-aminobenzylpenicillin used in the examples which follow contains about 14% of water, but anhydrous α-aminobenzylpenicillin (compare U.S. Pat. No. 3,144,445) can also equally well be used.

The α-amino-p-hydroxybenzylpenicillin used in the examples contains about 13% of water, but anhydrous α-amino-p-hydroxybenzylpenicillin can also equally well be used.

The 7-(α-amino-phenylacetamido)-3-acetoxymethyl-ceph-3-em-4-carboxylic acid used in the examples contains 8% of water, but anhydrous 7-(α-amino-phenylacetamido)-3-acetoxymethyl-ceph-3-em-4-carboxylic acid can also equally well be used.

The water content of the starting compounds is irrelevant in carrying out the process according to the invention.

By "ampicillin" is meant that α-aminobenzylpenicillin with the D=R-configuration in the side chain.

By "cephaloglycine" is meant that 7-(α-amino-phenylacetamido)-3-acetoxymethyl-ceph-3-em-4-carboxylic acid with the D=R-configuration in the side chain.

Explanation of the abbreviations used in the examples:

NMR=Nuclear Magnetic Resonance spectrum data
s=singlet
m=multiplet
AB=AB system
pts. by wt.=parts by weight
pts. by vol.=parts by volume
hrs.=hours
hr.=hour
THF=tetrahydrofuran
ether=diethyl ether
ethyl acetate=acetic acid ethyl ester
room temperature=about 20° C.
abs.=absolute
dcomp. pt.=decomposition point The percentage data for the yields denote yields in percent of theory.

All temperatures are in °C.

EXAMPLE 1 (Intermediate)

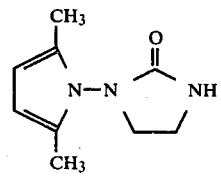

11.4 pts. by wt. of hexane-2,5-dione, 10.1 pts. by wt. of 1-amino-2-oxoimidazolidine (J. Amer. Chem. Soc.78, 5349 (1956)) and 0.2 wt. by wt. of p-toluenesulphonic acid in 200 pts. by vol. of benzene are refluxed overnight, the water of reaction being separated off via a separator. The mixture is concentrated and the residue is recrystallized from acetone. This gives 9.4 pts. by wt. of 1-(2,5-dimethylpyrrol-1-yl)-2-oxo-imidazolidine of melting point 166°–8°.

IR(KBr): 3,236, 1,720, 1,403, 1,265 and 760 cm$^{-1}$.

NMR(CD$_3$CN): s 5.67(2H), s(broad) 5.64(NH), A$_2$B$_2$3.63 and 3.50(4H) and s 2.02(6H) ppm (δ).

MW 179.2: Mass Spectrum: m/e 179. Calculated: C 60.32 H 7.31 N 23.44. Found: C 60.1 H 7.2 N 23.2.

EXAMPLE 2 (Intermediate)

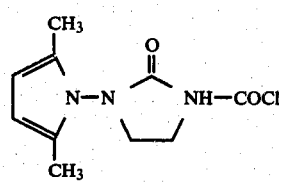

5.5 pts. by wt. of phosgene are added to a solution, cooled to −15°, of 9.0 pts. by wt. of 1-(2,5-dimethylpyrrol-1-yl)-2-oxo-imidazolidine in 100 pts. by vol. of abs. ethyl acetate, under a nitrogen atmosphere. 10.0 pts. by wt. of tri-n-butylamine dissolved in 30 pts. by vol. of abs. ethyl acetate are then added dropwise at 0°–5°. The mixture is stirred at 0° for 1 hr. and at room temperature for 4 hrs. The small amount of insoluble material is filtered off and the residue is concentrated. This gives 25.6 pts. by wt. of 1-chlorocarbonyl-2-oxo-3-(2,5-dimethyl-pyrrol-1-yl)-imidazolidine mixed with tributylammonium chloride, which does not need to be removed since it does not interfere with the subsequent reaction.

IR (liquid paraffin): 1,800 cm$^{-1}$.

EXAMPLE 3

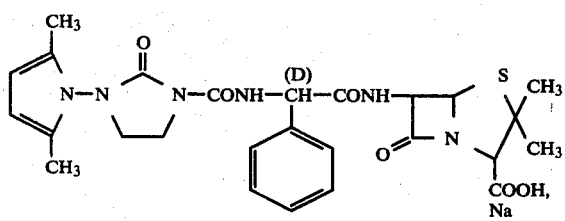

28.8 pts. by wt. of ampicillin trihydrate are dissolved, at 5°–10°, in 500 pts. by vol. of 80 percent strength aqueous THF by adding 4 percent strength sodium hydroxide solution. During this procedure, the pH should not exceed 8.3. 12.8 pts. by wt. of the acid chloride of Example 2 are added in portions to this solution, the pH being maintained between 7.3 and 7.5 by the successive addition of 2 percent strength sodium hydroxide solution. When no further sodium hydroxide solution is consumed, the small amount of insoluble material is filtered off and 500 pts. by vol. of water are added to the filtrate. The THF is stripped off and the aqueous phase which remains is extracted once with ethyl acetate. The aqueous solution is cooled to 5°, covered with a layer of cold ethyl acetate, acidified and extracted several times with ethyl acetate. The combined ethyl acetate extracts are dried over magnesium sulphate and concentrated. The residue is dissolved in 20 pts. by vol. of methanol and 18.5 pts. by vol. of a 1 M methanolic sodium caprylate solution are added. This solution is poured slowly into 300 pts. by vol. of ether, which contains 5% of methanol, whereupon the product precipitates. It is filtered off, washed with ether and dried over P$_2$O$_5$. This gives 8.2 pts. by wt. of sodium 6-{D-α-[(2-oxo-3-{2,5-dimethylpyrrol-1-yl}-imidazolidin-1-yl)carbonylamino]-phenylacetamido}-penicillanate, of dcomp. pt. 215°–220°.

IR(KBr): 1,760, 1,730, 1,595, 1,525, 1,385 and 1,255 cm$^{-1}$.

NMR(CD$_3$OD): m7.3(5H), s 5.68(2H), s 5.53(1H), AB 5.46 and 5.37(2H), s 4.12(1H), m centered at 3.85(4H), s 2.10(3H), s 3.05(3H), s 1.53(3H) and s 1.47(3H) ppm (δ).

EXAMPLE 4

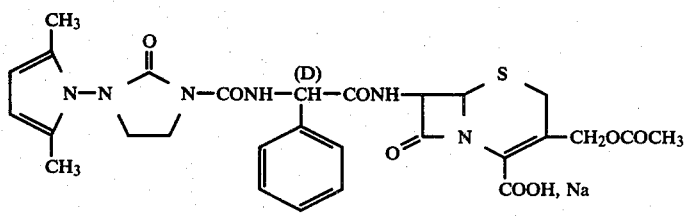

31.6 pts. by wt. of cephaloglycine dihydrate and 12.8 pts. by wt. of the acid chloride from Example 2 are reacted as in Example 3. This gives 8.9 pts. by wt. of sodium 7-{D-α-[(2-oxo-3-{2,5-dimethylpyrrol-1-yl}-imidazolidin-1-yl)-carbonyl-amino]-phenylacetamido}-3-acetoxymethyl-ceph-3-em-4-carboxylate of dcomp. pt. 190°–200°.

NMR (CD$_3$OD/D$_2$O): m 7.35(5H, s, 5.72(2H), AB 5.50 and 4.88(2H), AB 5.95 and 5.80(2H), A$_2$B$_2$ 3.92 and 3.80(4H), s 2.12 (3H), s 2.10(3H) s 2.01(3H) ppm (δ). All further protons are obscured, inter alia, by the solvent peak and by the signal of the replaceable protons.

IR(KBr): 1,760, 1,730, 1,665, 1,600, 1,385, 1,255 and 1,220 cm$^{-1}$.

It will be appreciated that the instant specification and examples are set forth by way of illustration and not limitation, and that various modifications and changes may be made without departing from the spirit and scope of the present invention.

What we claim is:

1. A β-lactam compound of the formula

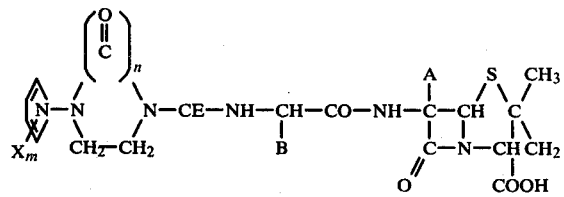

in which

A is hydrogen or methoxy,

B is phenyl; phenyl substituted by at least one of hydroxyl, halogen, methoxy, —CN and CH$_3$—SO$_2$—; thienyl; cyclohexenyl; 1,4-cyclohexadien-1-yl; or furyl;

E is oxygen or sulphur;

n is 1 or 2,

X is lower alkyl, trifluoromethyl, lower alkyl sulfonyl or lower alkyl thio, and m is 0,1 or 2, or a pharmaceutically acceptable salt thereof.

2. A compound according to claim 1, in which
A is hydrogen,
B is phenyl, hydroxyphenyl or 1,4-cyclohexadien-1-yl, and
E is oxygen.
3. A compound according to claim 1, in the form of the sodium salt.
4. A compound according to claim 1, of the formula

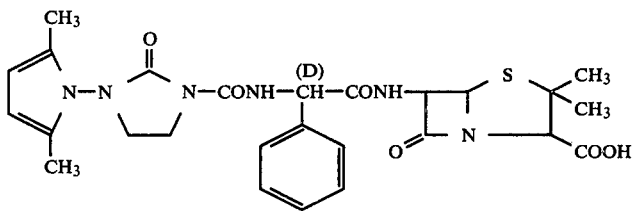

or a salt thereof.

5. An antibacterial composition containing as an active ingredient an antibacterially effective amount of a compound according to claim 1 in admixture with a solid or liquid diluent.
6. A medicament in dosage unit form comprising a tablet, pill, dragee, capsule, ampule or suppository comprising a composition according to claim 5.
7. A method of combating bacterial infections in human and non-human animals which comprises administering to the animals an antibacterially effective amount of a compound according to claim 1.

* * * * *